US00PP28888P2

(12) United States Plant Patent
Woolley

(10) Patent No.: US PP28,888 P2
(45) Date of Patent: Jan. 23, 2018

(54) ***BUXUS* PLANT NAMED 'SB 108'**

(50) Latin Name: *Buxus microphylla*
Varietal Denomination: SB 108

(71) Applicant: Rollin Edgerton Woolley, Gloucester, VA (US)

(72) Inventor: Rollin Edgerton Woolley, Gloucester, VA (US)

(73) Assignee: SAUNDERS BROTHERS, INC., Piney River, VA (US)

( * ) Notice: Subject to any disclaimer, the term of this patent is extended or adjusted under 35 U.S.C. 154(b) by 43 days.

(21) Appl. No.: 14/999,460

(22) Filed: May 9, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Penny J. Aguirre

(57) ABSTRACT

A new cultivar of *Buxus microphylla*, 'SB 108', that is characterized by its obovate-shaped leaves that are dark green in color with a waxy surface texture, its good resistance to boxwood blight and some resistance to boxwood leafminer, and its compact plant habit.

2 Drawing Sheets

Botanical classification: *Buxus microphylla.*
Variety denomination: 'SB 108'.

BACKGROUND OF THE INVENTION

The present invention relates to a new and distinct cultivar of *Buxus microphylla* and will be referred to hereafter by its cultivar name, 'SB 108'. 'SB 108' is a new cultivar of boxwood grown for use as a landscape and ornamental shrub.

The new cultivar of *Buxus* was discovered as a chance seedling in a garden by the Inventor in summer of 1989 in Williamsburg, Va. The parents are unknown. After further evaluation, The Inventor selected 'SB 108' as a unique plant in 2005.

Asexual propagation of the new cultivar was first accomplished by the Inventor using stem cuttings in Gloucester, Va. in September of 2005. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'SB 108' as a unique cultivar of *Buxus*.

1. 'SB 108' exhibits leaves that are dark green in color.
2. 'SB 108' exhibits leaves that have a waxy surface texture.
3. 'SB 108' exhibits good resistance to boxwood blight and some resistance to boxwood leafminer.
4. 'SB 108' exhibits leaves that are obovate in shape.
5. 'SB 108' exhibits a compact plant habit.

The new *Buxus* can be most closely compared to the *Buxus microphylla* var. *japonica* cultivars 'Green Beauty' (not patented) and 'Jim Stauffer' (not patented). 'Green Beauty' is similar to 'SB 108' in having a plant habit that is round in shape and in having leaves that are dark green in color with a waxy surface texture. 'Green Beauty' differs from 'SB 108' in having low resistance to boxwood leafminer (*Monarthropalpus flavus*) and in having leaves that are rounder in shape. 'Jim Stauffer' is similar to 'SB 108' in having leaves that are green in color with a glossy surface. 'Jim Stauffer' differs from 'SB 108' in having a less compact plant habit, and in having leaves that are rounder in shape, lighter green in color and less waxy in surface texture.

BRIEF DESCRIPTION OF THE DRAWINGS

The accompanying colored photographs illustrate the overall appearance and distinct characteristics of 6 year-old plants as field grown outdoors in Roseland, Va.

The photograph in FIG. 1 is a side view and illustrates the overall plant habit and appearance of 'SB 108'.

Figure 1:
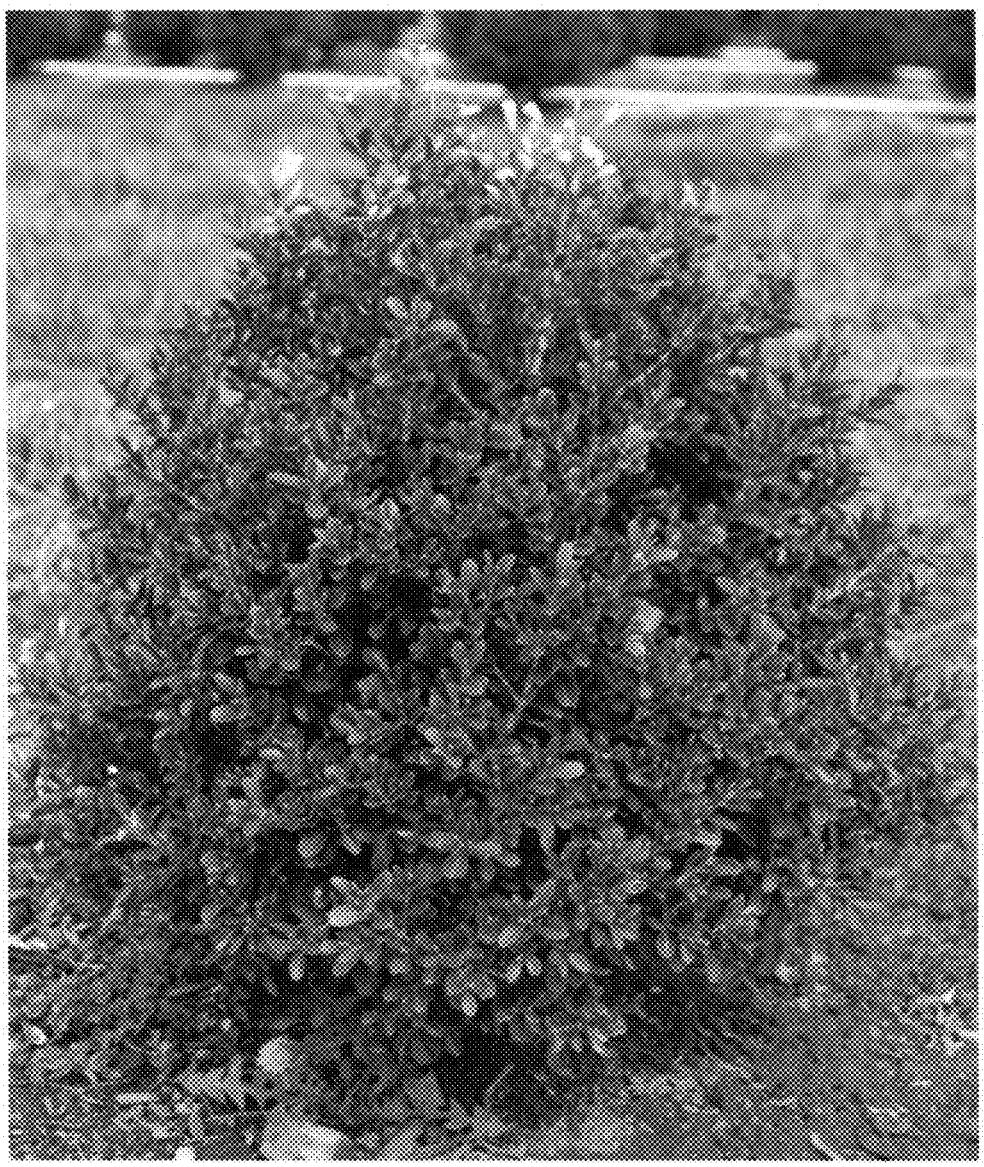
Figure 2:
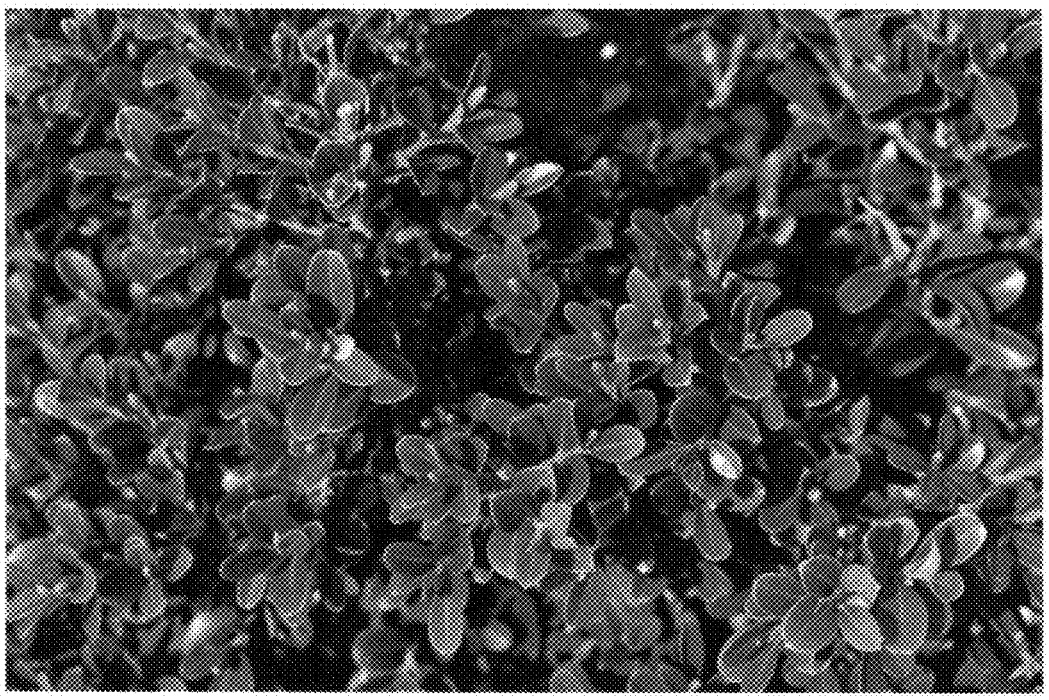

The photograph in FIG. 2 provides a close up view of the foliage of 'SB 108'.

The colors in the photographs are as close as possible with the photographic and printing technology utilized and the color values cited in the Detailed Botanical Description accurately describe the colors of the new *Buxus.*

DETAILED BOTANICAL DESCRIPTION

The following is a description of plants about 2 years in age from rooted cuttings as grown in one-gallon containers in an unheated poly greenhouse in Piney River, Va. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Evergreen, perennial shrub.

*Plant habit.*—Compact, upright, dense.

*Height and spread.*—A 15 year old plant reaches up to 91 cm in height and width in the landscape.

*Cold hardiness.*—At least to U.S.D.A. Zones 6 to 8.

*Diseases resistance.*—Exhibits good resistance to boxwood blight (caused be *Cylindrocladium buxicola*) and some resistance to boxwood leafminer (caused by *Monarthropalpus flavus*).

*Root description.*—Fibrous and fine, 161A in color.

*Root development.*—Roots initiate in about 30 days and fully develop as a young plant in a liner suitable for transplanting into a one-gallon container in about 9 months.

*Propagation.*—Stem cuttings.

*Growth rate.*—Moderate.

Stem description:

*Shape.*—Round to slightly quadrangular.

*Stem color.*—Young stems, mid-section and top of lateral stems and mid-section and top of tertiary stems; a blend of 146B and 144A; mature stems, base of lateral stems and base of tertiary stems; underlay of 144B and bark like, rugose overlay of 157A.

*Stem size.*—Main stems; average of 6 cm in length and 5 mm in diameter, lateral branches emerging from main stems; average of 10 cm in length and 4 mm in diameter, tertiary branches emerging from the lateral branches; average of 5 to 8 cm in length and 2 mm in diameter.

*Stem strength.*—Strong.

*Stem surface.*—New growth, mid-section and top of lateral and mid-section and top of tertiary branches; smooth, glabrous and shiny, mature and main stems, base of lateral stems and base of tertiary stems; rugose, dull, bark-like.

*Branch number.*—An average of 3 main stems, average number of branches per main stem; an average of 3 lateral branches emerging from main stems and an average of 16 tertiary branches emerging from the lateral branches.

*Branching habit.*—Stems arise from base, main branches held at an average angle of 0°, lateral branches held at an average angle of 20° to 30° (0°=horizontal).

Foliage description:

*Leaf shape.*—Obovate.

*Leaf division.*—Simple.

*Leaf base.*—Attenuate.

*Leaf apex.*—Varying between rounded and retuse.

*Leaf fragrance.*—None.

*Leaf venation.*—Pinnate, midrib is conspicuous on lower surface only (157A in color), matches leaf color on upper surface.

*Leaf margins.*—Entire.

*Leaf arrangement.*—Opposite.

*Leaf attachment.*—Sessile.

*Internode length.*—Up to 1 cm in length on main stems, up to 7 mm in length on lateral and tertiary branches.

*Leaf surface.*—Glabrous and shiny on upper surface, glabrous and slightly glossy, more dull on lower surface.

*Leaf texture.*—Slightly thick, tough and waxy.

*Leaf size.*—Up to an average of 2.5 cm in length and 1.2 cm in width.

*Leaf quantity.*—Average of 52 on a branch 10 cm in length.

*Leaf color.*—Young leaves; upper and lower surface 144A, mature leaves; upper surface NN137A, lower surface; 144A with thin margins 137A.

Inflorescence description: Flower initiation and development has not been observed to date.

It is claimed:

1. A new and distinct cultivar of *Buxus* plant named 'SB 108' as herein illustrated and described.

* * * * *